United States Patent [19]

Campbell

[11] Patent Number: 4,784,955

[45] Date of Patent: Nov. 15, 1988

[54] IMMUNOGEN CONJUGATES AND THE USE THEREOF IN A DIHYDROPYRIDINE ASSAY

[75] Inventor: Kevin P. Campbell, Iowa City, Iowa

[73] Assignee: Miles Inc., Elkhart, Ind.

[21] Appl. No.: 825,572

[22] Filed: Feb. 3, 1986

Related U.S. Application Data

[63] Continuation-in-part of Ser. No. 653,699, Sep. 21, 1984, abandoned.

[51] Int. Cl.[4] ............... G01N 33/531; G01N 33/537; G01N 33/577
[52] U.S. Cl. ........................ 435/172.2; 435/240.27; 435/948; 436/538; 436/543; 436/547; 436/548; 436/808; 436/815; 436/822; 530/387; 530/403; 530/404; 530/405; 530/406; 530/807; 530/808; 935/104; 935/110
[58] Field of Search .................. 435/192.2, 240, 948, 435/27; 436/518, 536, 538, 543, 547, 548, 808, 815, 822; 530/387, 403–406, 807–809; 935/110, 104

[56] References Cited

U.S. PATENT DOCUMENTS 4,404,278 9/1983 Hu et al. ........................... 436/547

OTHER PUBLICATIONS

J. C. Venter et al, *Journ. Biol. Chem.* 258, 9344–9348, 1983.

*Primary Examiner*—Sidney Marantz
*Assistant Examiner*—David A. Saunders
*Attorney, Agent, or Firm*—E. P. Gray; M. G. Boguslaski

[57] ABSTRACT

Disclosed are 1,4-dihydropyridine immunogen conjugates of immunogenic carrier materials coupled to a 1,4-dihydropyridine derivative. Said conjugates are useful for the preparation of antibodies thereto which antibodies may be used in immunoassays for 1,4-dihydropyridine compounds. An affinity column useful for the purification of said antibodies is also disclosed.

14 Claims, No Drawings

IMMUNOGEN CONJUGATES AND THE USE THEREOF IN A DIHYDROPYRIDINE ASSAY

This application is a continuation-in-part of application Ser. No. 653,699, filed Sept. 21, 1984 now abandoned.

BACKGROUND OF THE INVENTION $Ca^{2+}$ channel blockers are widely used for the treatment of various cardiovascular disorders. Nifedipine, nitrendipine, nisoldipine, nimodipine and related 1,4-dihydropyridines (hereafter alternatively referred to as DHPs) are the most potent class of $Ca^{2+}$ channel blockers. Radioreceptor and high performance liquid chromatography assays are available for the measurement of these agents in human serum, however, such techniques are cumbersome and costly and are not readily amenable to large-scale use.

The present invention provides immunogen conjugates comprising a DHP derivative coupled to immunogenic carrier materials and antibodies prepared against such immunogen conjugates. Such antibodies are useful in immunoassays for determining DHPs in biological fluids, thus filling the need for a rapid and sensitive assay for large-scale clinical use.

DESCRIPTION OF PERTINENT ART

Janis, et al (*J. Clin. Pharmacol.*, 1983; 23: 266–273) describe the development of radioreceptor and high performance liquid chromatographic assays for the calcium channel antagonist nitrendipine in serum samples. Krol, et al, *J. Chromatography*, 1983 teach the use of gas and liquid chromatographic analysis of the calcium channel antagonist nimodipine in blood, plasma and cerebrospinal fluid.

Neither of these references describe or suggest the immunogen conjugates or the antibodies raised thereto disclosed in the present invention nor the use of said antibodies in immunoassays for 1,4-dihydropyridines.

SUMMARY OF THE INVENTION

The present invention discloses 1,4-dihydropyridine immunogen conjugates of immunogenic carrier materials coupled to a 1,4-dihydropyridine derivative. The immunogen conjugates disclosed are of the general formula:

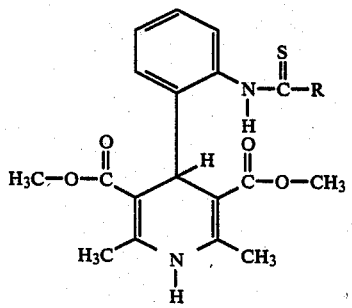

I wherein R is a protein or polypeptide.

Antibodies prepared against the immunogen conjugates of formula I and the use thereof in immunoassays are also taught.

Also disclosed is an affinity column useful for the purification of antibodies specific to 1,4-dihydropyridines from antiserum. Said affinity column is composed of 1,4-dihydropyridine-containing immunoadsorbent conjugates which are represented by the general formula:

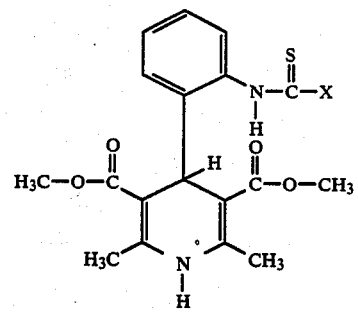

wherein X is an insoluble support matrix having a free available amino functional group.

The immunoadsorbent conjugates are used for purifying antibodies specific for 1,4-dihydropyridines from an antiserum containing said antibodies. The purification method includes the steps of: (a) incubating a mixture of said antiserum with a 1,4-dihydropyridine-containing immunoadsorbent conjugate thereby binding said antibodies to said conjugates; (b) washing the mixture of step (a) to remove nonspecifically bound material; and (c) dissociating said antibodies from said conjugate by incubating the mixture of step (a) at from about 0° C. to about 10° C. with a dissociative reagent thereby enhancing recovery of functional antibodies and isolating therefrom said antibodies.

DETAILED DESCRIPTION OF THE INVENTION

The DHP derivative which is used in the preparation of the immunogen conjugates is an affinity analog of nifedipine and is chemically, 1,4-dihydro-2,6-dimethyl-4-(2-isothiocyantophenyl)-3,5-pyridinedicarboxylic acid dimethyl ester (hereafter referred to as nifedipine-isothiocyanate) and is represented by the formula:

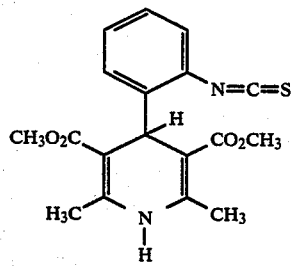

Nifedipine-isothiocyanate is commercially available from New England Nuclear Corp. or may be prepared as described by Venter, et al in *The Journal of Biological Chemistry* Vol. 258 (15) 9344–9348 (1983) which is incorporated herein by reference.

The nifedipine-isothiocyanate analog is covalently coupled to an immunogenic carrier material as described hereafter. The immunogenic carrier material may be a protein or polypeptide having available amino functional groups for coupling to the nifedipine-isothiocyanate derivative. When the immunogenic carrier is a proteinaceous material, said carrier is preferably incubated with nifedipine-isothiocyanate present in a sufficiently high concentration to form those immunogen conjugates having a ratio of nifedipine-isothiocyanate to carrier of about at least one to one. A sufficiently high concentration of nifedipine-isothiocyanate can be maintained by the inclusion of a sufficient amount of ethanol to maintain the solubility of the nifedipine-isothiocyanate during the incubation.

For the most part, immunogenic proteins and polypeptides will have molecular weights between 4,000 and 10,000,000 preferably greater than 15,000 and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. Further reference for the state-of-the-art concerning conventional immunogenic carrier materials and techniques for coupling haptens thereto may be obtained from the following (each of which are incorporated herein by reference): Parker, *Radioimmunoassay of Biologically Active Compounds*, Prentice-Hall (Englewood Cliffs, N.J. U.S.A., 1976); Butler, *J. Immunol. Meth.*, 7:1–24 (1974); Weinryb and Shroff, *Drug Metab. Rev.*, 10:271–283 (1975); Broughton and Strong, *Clin. Chem.*, 22:726–732 (1976); and Playfair, et al, *Br. Med. Bull.*, 30:24–31 (1974). Preferred proteins for use as immunogenic carrier materials are bovine serum albumin, casein, ovalbumin and keyhole limpet hemocyanin. Particularly preferred is keyhole limpet hemocyanin.

Preparation of specific antibodies using the present immunogen conjugates may follow any conventional technique. Numerous texts are available describing the fundamental aspects of inducing antibody formation. For example, see Parker, *Radioimmunoassay of Biologically Active Compounds*, Prentice-Hall (Englewood Cliffs N.J., U.S.A., 1976) which is incorporated herein by reference. In the usual case, a host animal such as a rabbit, goat, mouse, guinea pig, sheep or horse is injected at one or more of a variety of sites with the immunogen conjugate, normally in admixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. The antiserum itself may then be used in performing the actual assays or purification steps may be taken to remove undesired material such as nonspecific antibodies and the like. Such purification techniques include the precipitation of an IgG fraction from the antiserum using ammonium sulfate or by purification of an affinity column from an insoluble 1,4-dihydropyridine-containing immunoadsorbent conjugate. Said, 1,4-dihydropyridine-containing immunoadsorbent conjugate may be, for example, those prepared as described hereafter from nifedipine-isothiocyanate and AH-Sepharose 4B or nifedipine-isothiocyanate and lysine-Sepharose 4B. Clearly, one skilled in the art will recognize that other support matrices having a free available amino functional group may be used to form an immunoadsorbent conjugate with nifedipine-isothiocyanate. Additionally, in order to prevent the immunoadsorbent conjugate from acting as an ion exchanger, the residual functional primary amine groups of the selected support matrix (e.g., AH-Sepharose 4B, lysine-Sepharose 4B and the like) left after the coupling of the nifedipine-isothiocyanate may be blocked by acetylation utilizing a water-soluble carbodiimide as described, infra. Said carbodiimide is preferably 1-ethyl-3-(3-dimethyl-aminopropyl)-carbodiimide (available from Sigma).

The 1,4-dihydropyridine-containing immunoadsorbent conjugate is then used to purify antibodies from an antiserum containing the antibodies as follows. The antiserum containing the 1,4-dihydropyridine-specific antibodies is incubated with the desired immunoadsorbent conjugate (preferably a conjugate prepared from nifedipine-isothiocyanate and AH-Sepharose 4B or nifedipine-isothiocyanate and lysine-Sepharose 4B) which serves to bind said 1,4-dihydropyridine-specific antibodies to the conjugate. This mixture is then washed to remove non-specifically bound materials with, for example, phosphate buffered saline or a sodium chloride solution. Following the washing, the mixture is then incubated with a solution capable of dissociating the bound antibodies from the immunoadsorbent conjugate. This solution may be any such solution capable of affecting such dissociation while still serving to enhance the recovery of functional antibodies. Preferred for such dissociation is an alkaline solution containing sodium chloride and dioxane. Particularly preferred is a solution of about pH 11, containing about 1 M sodium chloride, about 50 mM diethylamine and about 10 percent dioxane. Also partcularly preferred is a solution of about 50 mM sodium phosphate (about pH 7.4), about 1 M sodium chloride, from 0 to about 10 percent dioxane and about $1-2 \times 10^{-4}$ M of diethyl 1,4-dihydro-2,4,6-trimethyl-3,5-pyridine dicarboxylate. The incubation may be carried out at about 0° C. to about 10° C., preferably at about 0° C. to about 4° C. Isolation of the dissociated antibodies is then achieved by conventional techniques.

Initial testing for the presence of the DHP-specific antibody may be carried out using an indirect immunoperoxidase staining of the immunogen conjugates as follows. Control (unlabeled) proteins and nifedipine-protein immunogen conjugates (different from the carrier nifedipine-protein conjugate used for immunization), are either dotted onto nitrocellulose paper or transferred following SDS gel electrophoresis onto nitrocellulose paper. The nitrocellulose blot is then incubated with the test antiserum followed by a secondary antibody conjugated to peroxidase and then developed with a peroxidase substrate. Positive antisera will react with the nifedipine-protein conjugate but not with the unlabeled protein.

The polyclonal antibodies prepared against the immunogen conjugates have been found to provide excellent specificity. Inactive metabolites of nitrendipine as well as structurally unrelated calcium channel blockers verapamil and diltiazem do not cross-react with said antibodies. Further, one skilled in the art will readily appreciate that monoclonal antibodies for specific 1,4-dihydropyridines may be prepared by standard techniques such as described hereafter.

Preferably, the antibodies derived from the immunogen conjugates are to be used in a radioimmunoassay (RIA) for determining the quantity of DHP present in a biological sample. However, it is well-known that such antibodies are also required in various other assays. These assays, which are contemplated equivalents to the radioimmunoassay described hereinafter, include heterogeneous and homogeneous enzyme-labeled binding assays, fluorescence-labeled binding assays, and chemiluminescence-labeled binding assays. Such assays may be used for determining the concentration of any dihydropyridine in a biological sample such as nitrendipine, nifedipine, nisoldipine, nimodipine and the like.

The RIA for the 1,4-dihydropyridines is based on the competition between 1,4-dihydropyridines in a biological sample and a fixed quantity of radiolabeled-1,4-dihydropyridine such as radiolabeled-nitrendipine (i.e., 2,6-dimethyl-3-carboethoxy-5-carbomethoxy-4-(3-nitrophenyl)-1,4-dihydropyridine) to an antibody which has a high specificity and affinity for the 1,4-dihydropyridines. The radiolabeled nitrendipine can be labeled in any manner well-known in the art with any suitable radionuclide. A listing of the radionuclides which are now conventionally in use in reagents and which may be used in this invention are listed in the index of radionuclides found on page 81 of the 1978 edition of the Catalogue of the New England Nuclear Corporation, Boston, Mass, U.S.A., (New England Nuclear, 1977) incorporated herein by reference. Among radionuclides which may be utilized include the following: hydrogen-3 (tritium) and the radioisotopes of iodine ($^{123}$I, $^{124}$I, $^{125}$I, $^{126}$I, $^{128}$I, $^{130}$I, $^{1331}$I and $^{132}$I) with $^3$H being preferred from considerations of availability, half life and specific activity and/or the ability of these to be readily detected using a conventional liquid scintillation counter.

The RIA can be performed by any manner known in the art. For example, the antiserum containing the antibody prepared against the immunogen conjugate (or alternatively the Ig fraction obtained by ammonium sulfate purification or the affinity purified antibody) can be diluted to a suitable concentration with a buffer containing the radiolabeled nitrendipine (or other radiolabeled 1,4-dihydropyridine) and incubated under suitable conditions until equilibrium is reached with either the biological sample to be determined (i.e., blood or fractions thereof, saliva, urine and the like) or a standard solution used for preparing a standard curve. Separation of the 1,4-dihydropyridine bound to antibody from the free 1,4-dihydropyridine is effected by well-known procedures such as by the use of dextran-coated charcoal, Protein A Sepharose beads, the double antibody method and the like. Preferably, the separation is achieved using dextran-coated charcoal. The radioactivity of one of the separated substances is counted by, for example, a well-type scintillation counter and a standard curve is prepared based on the value obtained for standard solutions assayed by the same technique. The DHP level in the biological sample being tested is then determined based on that standard curve.

Additionally, the radioimmunoassay may be carried out utilizing conjugates of the 1,4-dihydropyridine-specific antibody (either polyclonal or monoclonal) covalently coupled to an insoluble support such as Sepharose 6MB beads to form an immunoadsorbent matrix. This matrix can then be used in the competitive binding assay to bind the radiolabeled 1,4-dihydropyridine with high affinity, thus facilitating separation from the assay medium as by mild centrifugation. The amount of radiolabeled 1,4-dihydropyridine bound to the antibody of the conjugate may then be readily determined as described above.

Also provided within the scope of the present invention is a test kit such as a mercantile unit in order to carry out an immunoassay for a particular DHP. Such kits will include one or more containers such as microtiter plates, solid supports, test tubes, trays and the like as well as antisera, for example in freeze dried form. The kit may also contain standard amounts of a DHP whereby a standard curve may be constructed, containers for holding any necessary reagents for inducing an observable or otherwise measurable reaction and so on. Clearly, the skilled artisan can prepare a kit suitable for use in any particular immunoassay, the precise physical embodiment of which will depend upon the type assay contemplated.

The following examples are set forth as a means of illustrating the present invention and are not to be construed as a limitation thereon.

EXAMPLE 1

Preparation of Immunogen Conjugates

Nifedipine-isothiocyanate (1,4-dihydro-2,6-dimethyl-4-(2-isothiocyanatophenyl)-3,5-pyridinedicarboxylic acid dimethyl ester) obtained from New England Nuclear was coupled to bovine serum albumin as follows. Bovine serum albumin (10 mg) was dissolved in 10 ml of 100 mM sodium bicarbonate (pH 9.0) and then incubated with 0.6 mg of nifedipine-isothiocyanate (dissolved in ethanol to make the final concentration of ethanol in the incubation medium 0.65 percent) for 24 hours at room temperature with shaking in the dark which thus formed the desired nifedipine-isothiocyanate bovine serum albumin immunogen conjugate. The formation of said conjugate was monitored by including [$^3$H]nifedipine-isothiocyanate in the preparation of the bovine serum albumin-nifedipine conjugate. Bovine serum albumin--[$^3$H]nifedipine conjugate (10–40 micrograms) was separated from free nifedipine by SDS-polyacrylamide gel electrophoresis and [$^3$H]nifedipine incorporation was detected by fluorography or gel slice analysis. Gel slices (2.5 mm) were digested overnight at 45° C. in 0.8 ml of 30% hydrogen peroxide before liquid scintillation fluid was added. Radioactivity was measured using a Beckman LS8100 counter.

Nifedipine-isothiocyanate was also coupled to casein, ovalbumin and keyhole limpet hemocyanin using the procedures described above. An alternate procedure for the coupling of nifedipine-isothiocyanate to various proteins (i.e., bovine serum albumin, ovalbumin, casein and keyhole limpet hemocyanin) was to dissolve the protein (20 mg) in 2 ml of 100 mM sodium bicarbonate (pH 9.0) and then incubate with 0.8 mg of nifedipine-isothiocyanate (dissolved in ethanol to make the final concentration of ethanol in the incubation medium 38 percent) for 24 hours at 37° C. with shaking in the dark. This alternate procedure is useful for producing nifedipine conjugates at high protein concentrations.

EXAMPLE 2

Production and Isolation of Antibodies

In order to raise antibodies against the 1,4-hydropyridines, a bovine serum albumin-nifedipine iothiocyanate immunogen conjugate was used directly for immunization or was cross-linked with 0.04% glutaraldehyde for eight hours at room temperature prior to immunization of rabbits. In either case, the immunogen conjugate was emulsified in an equal volume of Freund's complete adjuvant.

New Zealand white rabbits were bled to obtain preimmune sera and were then immunized intramuscularly and intradermally at multiple sites along the back and legs. Rabbits received 0.5 milligram (mg) of bovine serum albumin-nifedipine isothiocyanate immunogen conjugate in Freund's complete adjuvant on day 0 followed by 0.5 mg insults in Freund's incomplete adjuvant every 2-3 weeks. Rabbits were bled after their third immunization every two weeks. Blood was withdrawn from the ear vein, allowed to clot overnight at 4° C., and serum was isolated by centrifugation. In order to reduce the antibodies produced to bovine serum albumin, subsequent immunizations were carried out with keyhole limpet hemocyanin-nifedipine isothiocyanate immunogen conjugates. Using the procedures described above, casein-nifedipine isothiocyanate, ovalbumin-nifedipine isothiocyanate and keyhole limpet hemocyanin-nifedipine isothiocyanate immunogen conjugates were also used to immunize rabbits and isolate specific antibodies produced to the conjugates. The keyhole limpet hemocyanin-nifedipine isothiocyanate immunogen conjugate was mixed with an equal volume of aluminum hydroxide and phosphate buffered saline and stirred for 1 hour at 4° C. and then emulsified in an equal volume of Freund's complete adjuvant prior to use in the immunizations.

All of the above procedures were successful in obtaining high affinity 1,4-dihydropyridine-specific antibodies in rabbits. Keyhole limpet hemocyanin produced a response in the shortest time (4 weeks) and produced the highest titer antiserum of 1,4-dihydropyridine-specific antibodies. Bovine serum albumin-nifedipine isothiocyanate immunogen conjugate and the keyhole limpet hemocyanin-nifedipine isothiocyanate immunogen conjugate were also used in the immunization of sheep to produce anti-1,4-dihydropyridine antibodies.

1,4-dihydropyridine-specific antibody was partially purified from antisera by a 50% ammonium sulfate precipitation in the cold for 24 hours. The precipitated IgG fraction was then resuspended in phosphate buffered saline and dialysed against phosphate buffered saline in the cold for 24 hours.

EXAMPLE 3

Preparation of Nifedipine-Sepharose Affinity Column

Nifedipine-isothiocyanate obtained from New England Nuclear was coupled to aminohexyl-Sepharose 4B (i.e., AH-Sepharose 4B) obtained from Pharmacia as follows. Nifedipine-isothiocyanate (5 mg) in 10 ml of 95% ethanol was added to 5 g of preswollen and washed AH-Sepharose 4B in 100 ml of 20 mM sodium bicarbonate (pH 8). This mixture was shaken at 37° C. overnight. The resulting nifedipine-Sepharose 4B immunoadsorbent conjugate was then washed three times with 100 ml of 1 M TRIS buffer (pH 7.5) followed by exhaustive washing with 150 mM NaCl, 10 mM TRIS (pH 7.2). The amount of nifedipine-isothiocyanate incorporated was conveniently monitored by adding 5 μl of [$^3$H] nifedipine-isothiocyanate (83 Ci/mmole) as a tracer to the above coupling reaction.

In order to prevent the immunoadsorbent conjugate from acting as an ion exchanger, residual functional primary amine groups of the AH-Sepharose 4B material left after the coupling of nifedipine-isothiocyanate were blocked by acetylation as follows. The nifedipine-Sepharose 4B immunoadsorbent conjugate was washed with water followed by 50% (v/v) dimethylformamide and 250 mM sodium acetate (pH 4.75). Then 50% (v/v) dimethylformamide, 250 mM sodium acetate (pH 4.75) was added to a final volume of 5 ml/ml of nifedipine-Sepharose 4B immunoadsorbent conjugate. To this was added water soluble 1-ethyl- 3-(3-dimethylaminopropyl) carbodiimide as a powder to a final concentration of 100 mM. The resulting mixture was then allowed to react overnight at 30° C. with end-over-end mixing, followed by extensive washing with phosphate buffered saline before use.

The amount of nifedipine-isothiocyanate coupled to the AH-Sepharose 4B was determined by counting a measured quantity of washed, suspended immunoadsorbent conjugate in liquid scintillation fluid in a scintillation counter. The degree of coupling was controllable by varying the concentration of the nifedipine-isothiocyanate and the pH of the coupling mixture. It was determined that the greatest efficiency of coupling was obtained at pH 10.

By following substantially similar techniques, nifedipine-isothiocyanate was coupled to lysine-Sepharose 4B with subsequent blocking of residual reactive amine groups as described above.

EXAMPLE 4

Affinity Purification of Nifedipine-Specific Antibodies

The nifedipine-Sepharose 4B affinity column (1.0 ml packed column) prepared as described in Example 3 was incubated with 100 ml sheep anti-nifedipine serum for 24 hours at room temperature, with gentle shaking. The affinity column was then washed extensively with phosphate buffered saline and then 1 M NaCl. The nifedipine-specific antibodies were then dissociated (eluted) by incubation at about 0°-4° C. with 1M NaCl, 50 mM diethylamine (pH 11.5) and 10% dioxane. The eluted antibodies were quickly placed on a G-25M Sephadex column for desalting and were recovered in phosphate buffered saline thereby returning the antibodies to a neutral pH.

In an alternate procedure, the nifedipine-specific antibodies were eluted from the nifedipine-Sepharose 4 B affinity column by incubation with a solution of 50 mM sodium phosphate (pH 7.4), 1M NaCl, 10% dioxane and $2 \times 10^{-4}$ M diethyl 1,4-dihydro-2,4,6-trimethylpyridine dicarboxylate. (It was also possible to perform this elution in the absence of dioxane). Similarly, the eluted antibodies were rapidly placed on a G-25M Sephadex column for desalting and were recovered in phosphate buffered saline.

EXAMPLE 5

Immunoblot Characterization of the Prepared Polyclonal Antibodies

Unlabeled and nifedipine-labeled proteins were dotted onto nitrocellulose paper or transferred onto nitrocellulose paper following SDS polyacrylamide gel electrophoresis. Nitrocellulose blots were blocked with 0.05% Tween-20 or 3% bovine serum albumin in phosphate buffered saline for 1 hour at room temperature. Blots were then incubated for 1 hour at room temperature with a 1:10 to 1:1000 dilution of test antisera in the presence of blocking agent. Following washing, the blots were incubated for 1 hour with a 1:1000 dilution of goat anti-rabbit IgG peroxidase conjugate. Blots were then developed with 4-chloro-1-naphthol following washing. Specificity for the staining was shown using the unlabeled proteins as controls and/or by including $10^{-7}$ M nitrendipine in the primary incubation with the test antisera.

The experimental data indicated that the prepared antibody recognized nifedipine coupled to carbonic anhydrase while it did not react with unlabeled carbonic anhydrase.

EXAMPLE 6

1,4-Dihydropyridine Radioimmunoassay

The radioimmunoassay of a sample containing an unknown amount of 1,4-dihydropyridine was performed using 1.5 ml Eppendorf tubes in the dark. 1,4-dihydropyridine standards were prepared daily by serial dilution in 0.1% bovine serum albumin in saline and stored at 4° C. in the dark. 1,4-dihydropyridine-specific antibodies were prepared as described in Example 2 or were affinity purified as described in Example 4. A titer test was then performed with the 1,4-dihydropyridine-specific antibody using a fixed amount (for example 20 pM) of [$^3$H]nitrendipine (obtained from New England Nuclear) to determine the dilution needed for binding 50% of the added [$^3$H]nitrendipine.

Each assay tube contained a 0.1 ml aliquot of sample or standard and 1 ml of the following assay medium: 150 mM NaCl, 10 mM TRIS (pH 7.2), 0.1% 3 nitrendipine and the appropriate gelatin, 20 pM [$^3$H]nitrendipine and the appropriate amount of antibody as determined by the titer test above. After a 1 hour incubation in the dark at room temperature, the assay tubes were transferred to an ice water bath for 10 min. Separation of free and antibody bound [$^3$H]nitrendipine was achieved by the addition of 0.2 ml of ice cold dextran-coated charcoal (i.e., 625 mg Norit A charcoal, 62.5 mg of Dextran T-70 and 100 ml of a mixture of 150 mM NaCl, 10 mM TRIS (pH 7.2) and 0.1% gelatin). After an additional 12 minutes in the ice bath, the assay tubes were centrifuged for 15 minutes at 850×g in a Beckman TJ-6 centrifuge. A 0.80 ml sample of the clear supernatant was then added to 10 ml of liquid scintillation fluid and counted in a Beckman LS8100 liquid scintillation counter. A standard curve was constructed by plotting the average percent $B/B_o$ (where B is [$^3$H]nitrendipine bound in the presence of an unknown amount of unlabeled 1,4-dihydropyridine and $B_o$ is the [$^3$H]nitrendipine bound in the absence of unlabeled 1,4-dihydropyridine) of the triplicate values of each standard on the linear axis of semi-logarithmic graph paper as a function of the concentration of the standards in picograms per milliliter. The average percent $B/B_o$ of the triplicate values of each sample and control was determined and the 1,4-dihydropyridine concentration from the standard curve was also determined. The nitrenedipine net counts per minute (CPM) and percent $B/B_o$ values are set forth in Table I. Similar standard curves were prepared for other 1,4-dihydropyridines.

TABLE I

| Nitrendipine Standard[a] (picograms/ml) | Net CPM | % $B/B_o$[b] |
|---|---|---|
| 0.0 | 1747 | 100.0 |
| 18.0 | 1492 | 85.4 |
| 36.0 | 1406 | 80.5 |
| 72.0 | 1024 | 58.6 |
| 180.0 | 673 | 38.5 |
| 360.0 | 482 | 27.6 |
| 720.0 | 346 | 19.8 |
| 1800.0 | 225 | 12.9 |

[a]Concentration of nitrendipine standard in the final assay mixture.
[b]Defined in the text.

An alternate procedure for the RIA on human plasma samples involves the dilutions of standards in normal pooled human plasma (rather than in bovine serum albumin in saline, as described above) and the use of 0.2 ml aliquots of standard or human plasma samples. Separation of free and antibody bound [$^3$H]was also achieved by the use of dextran-coated charcoal of the following composition: 2.7 g Norit A charcoal, 270 mg of Dextran T-70 and 100 ml of a mixture of 150 mM NaCl, 10 mM TRIS (pH 7.2) and 0.1% gelatin.

EXAMPLE 7

Monoclonal Antibody Production

One-month old female BALB/c mice were immunized (intraperitoneal) with 0.5 mg of keyhole limpet hemocyanin-nifedipine isothiocyanate conjugate in Freund's complete adjuvant. After four weeks the mice were boosted three times with 0.5 mg of keyhole limpet hemocyanin-nifedipine isothiocyanate conjugate in Freund's incomplete adjuvant. Mice were bled after their third immunization. Blood was withdrawn from the tail and antiserum was isolated by centrifugation. Serum samples were tested to insure a high titer of antibody against the 1,4-dihydropyridines using a [$^3$H]nitrendipine binding assay (described below) and an indirect immunoblot assay as taught in Example 5.

Hybridoma cells were produced by fusing NS-1 mouse myeloma cells with spleen cells from an immunized mouse using a modification of the technique described by Kennett et al (Kennett, R. H., McKearn, T. J., Bechtol, K. B., eds., 1980, *Monoclonal Antibodies Hybridomas: A New Dimension in Biological Analyses*, Plenum Press, New York, pp 365-367). The spleen was removed aseptically from an immunized mouse and transferred to a 120 mm petri dish containing 5 ml of HEPES buffered RPMI 1640 with 10% heat inactivated fetal calf serum (C-TCM). The spleen was teased apart in C-TCM making a single cell suspension and the suspension was then centrifuged at 1000 rpm for 5 minutes. The cell pellet was resuspended in 5 ml of C-TCM and the cells were counted. The mouse myeloma cells were prepared by harvesting 50-100 ml of NS1 cells (which were growing in a log phase of 400,000-700,000 cells per ml of medium) by centrifugation. The pelleted cells were resuspended in 5 ml of C-TCM and after appropriate dilutions the cells were counted. Spleen cells and NS1 cells were mixed at a ratio of 10:1 spleen cells to NS1 cells and incubated at 37° C. for 5 minutes. The mixed cell suspension was then centrifuged at 1000 rpm for 5 minutes and the supernate medium drawn off with a pipette. The tube was tapped gently to loosen the cell pellet. While maintaining the temperature of the cells at 37° C., 1.5 ml of 50% PEG 1500 was added over a 1 minute period. The treated cell mixture was maintained at 37° C. for an additional minute with gentle stirring. Immediately after incubation, 2 ml of HEPES buffered RPMI 1640 (no fetal calf serum) was added dropwise over a 2 minute period and an additional 8 ml of HEPES buffered RPMI 1640 (no fetal calf serum) was added over the next minute. The cells were then centrifuged at 1000 rpm for 5 minutes. The cell pellet was resuspended in 10 ml C-TCM and diluted to a final concentration of $2 \times 10^6$ cells/ml. The cell mixture was distributed into twenty 96-well microtiter plates (100 μl per well which resulted in $2 \times 10^5$ cells/well) and incubated at 37° C. Approximately 24 hours after plating, 100 μl of HAT medium (hypoxanthine-aminopterin-thymidine) in C-TCM was added to each well such that the final concentration of hypoxanthine was $1 \times 10^{-4}$M, aminopterin was $4 \times 10^{-7}$M and thymidine was $1.6 \times 10^{-5}$M.

After 10–14 days incubation, aliquots of the hybridoma culture supernatants were removed from the wells and the medium replaced with fresh C-TCM. The aliquots were assayed against a bovine serum albumin-nifedipine isothiocyanate conjugate using a immunodot screening assay on Millititer plates (Millipore Corp.). Millititer plates are 96-well plates with a nitrocellulose (0.45 μm) membrane sealed to the bottom. Bovine serum albumin-dihydropyridine conjugate (10 mg/ml) was dotted (0.5 μl) onto nitrocellulose in each well of the millititer plate and allowed to dry. The plates were then blocked with 3% BSA in TBS (i.e., 20 mM TRIS, 200 mM NaCl, pH 7.5) for 15 minutes. Following blocking of the nitrocellulose, hybridoma supernatants (50 μl) were placed in each well and incubated for 60 minutes. The plates were washed 5 times with TBS to remove unbound antibody, and blocked again in 3% BSA-TBS for 15 minutes. After blocking, the plates were incubated for 60 minutes with goat anti-mouse IgG-peroxidase linked secondary antibody (Cappel Laboratories) at 1:1000 dilution in 3% BSA-TBS. The plates were washed 5 times with TBS and developed using 4-chloro-1-naphthol (3 mg/ml cold methanol) as a substrate and hydrogen peroxide (0.015%) in 100 ml of room temperature TBS. A positive reaction for dihydropyridine-specific monoclonal antibody appeared as a purple/brown dot in the center of the well.

Wells having positive supernatants were examined for colonies. The colonies were removed from the wells with a disposable pipette and transferred to a fresh 96 well plate. When the cells filled the well of the 96 well plate they were transferred to a 24 well plate and the supernate screened again. When the cell number reached the point where the cells filled two wells of a 24 well plate, they were transferred to a T-25 flask and from there to a T-75 flask. Supernatants from T-75 flasks were then tested for dihydropyridine-specific antibodies using the immunoblot assay of Example 5. A [$^3$H]nitrendipine binding assay was carried out as follows.

The assay was performed in triplicate using 1.5 ml Eppendorf tubes in the dark. Each sample (1.0 ml) contained 150 mM NaCl, 10 mM TRIS (pH 7.2) 10–500 pM [$^3$H]nitrendipine, 1.0–10 μl antiserum or 10–100 μl hybridoma supernatant and 50 μl/ml anti-mouse IgG-Sepharose 4B beads (Cappel). After rotation overnight at 4° C. in the dark, the beads were collected by centrifugation and the supernatant was sampled. The beads were then washed three times in 150 mM NaCl and 10 mM TRIS (pH 7.2). [$^3$H]Nitrendipine was then measured using liquid scintillation counting in the initial supernatant (which represents the free [$^3$H]nitrendipine) and in the anti-mouse IgG-Sepharose beads (which represents the [$^3$H]nitrendipine bound to the antibody). Hybridoma colony XIIIE8$_2$, which produced the highest [$^3$H]nitrendipine binding activity, was then subcloned from the T-75 flask using limiting dilution analysis in 96 well microtiter plates. The supernatants from the dilution-cloned colonies were also screened using the immuno-dot assay. Positive dilution cloned colonies of XIIIE8$_2$ were then picked and cultured as described above. The monoclonal antibodies produced by the dilution cloned colonies were then purified to homogeneity directly from the culture medium using ammonium sulfate precipitation as follows.

The dilution cloned colony XIIIE8$_2$/H8 was grown in HB102 serum-free medium for 7–12 days. The culture medium was then collected by centrifugation for 5 minutes at 1000 rpm and then centrifuged for 1 hour at 10,000 rpm using a JA-10 rotor in a Beckman J2-21 centrifuge to remove cell debris. The pellet was discarded and the supernatant was mixed with an equal volume of filtered, saturated ammonium sulfate, pH 7.0. The pH was adjusted to 8.0 and the medium allowed to stir overnight at 4° C. The mixture was centrifuged again at 10,000 rpm for 35 minutes and the pellet rehomogenized in PBS (50 mM NaH$_2$PO$_4$, 0.9% NaCl, pH 7.4) and then placed on a PD-10 column (Pharmacia Fine Chemicals). Approximately 20–150 micrograms of pure monoclonal antibody were obtained from one milliliter of XIIIE8$_2$/H8 culture medium.

Hybridoma cell line XIIIE8$_2$/H8 has been deposited with the American Type Culture Collection and has been assigned accession number HB 8847.

Following substantially the same procedure as described above, the hybridoma XH4$_2$/G1 was prepared which produces a monoclonal antibody to the 1,4-dihydropyridine calcium channel blockers. The hybridoma cell line XH4$_2$/G1 has been deposited with the American Type Culture Collection and has been assigned accession number HB 8889.

EXAMPLE 8

Preparation of Anti-Dihydropyridine Antibody Columns

Monoclonal antibodies from hybridoma XIIIE8$_2$/H8 (or alternatively monoclonal antibodies from hybridoma XH4$_2$/G1 or affinity purified polyclonal antibodies) were covalently coupled to Sepharose 6MB beads to form an immunoadsorbent matrix as follows. One gram of freeze-dried cyanogen bromide-activated Sepharose 6MB was swollen for 15 minutes in 1 mM HCl and then washed with aliquots of HCl (a total of 200 ml was used) on a 50 ml glass filter (porosity F4). One gram of freeze-dried powder yielded approximately 3 ml of sedimented beads. Ten milligrams of the purified monoclonal antibody XIIIE8$_2$/H8 was dissolved with 3 ml coupling buffer (0.1M NaHCO$_3$, 0.5M NaCl, pH 8.3) and incubated with activated Sepharose 6MB for 18 hours at 4° C. to insure efficient coupling. The monoclonal antibody-Sepharose beads were washed three times with coupling buffer and incubated with 5 ml of 0.2M glycine (pH 8) for 2 hours at room temperature to block excess active groups. The monoclonal antibody-beads were then washed 3 times, each cycle consisting of a wash with 0.1M acetate, 0.5M NaCl (pH 4) followed by a wash with coupling buffer. The washed monoclonal antibody XIIIE8$_2$/H8-Sepharose beads (3 ml) were stored in 12 ml of phosphate buffered saline and were used in the radioimmunoassay of Example 9 with a bead to buffer ratio equal to 1:9.

EXAMPLE 9

1,4-Dihydropyridine Radioimmunoassay with Monoclonal Antibodies Conjugated to Sepharose 6MB Beads The radioimmunoassay of 1,4-dihydropyridine was performed in triplicate using 1.5 ml Eppendorf tubes in the dark. 1,4-dihydropyridine standards were prepared by serial dilution in 0.1% (or 0.5%) bovine serum albumin in saline or normal pooled human plasma and stored at 4° C. in the dark. A titer test was performed with various amounts of monoclonal antibody XIIIE8$_2$/H8-Sepharose beads (prepared as described in Example 8)

and 100 pM [³H]nitrendipine to determine the amount of beads needed for binding 40–70% of the added [³H]nitrendipine. Each assay tube contained a 0.1 ml aliquot of sample or standard and 1 ml of the following assay medium: 150 mM NaCl; 10 mM TRIS (pH 7.2); 0.1% gelatin; 100 pM [³H]nitrendipine; and 20 μl of monoclonal antibody XIIIE8₂/H8-Sepharose beads. After an overnight incubation in the dark at 4° C., the assay tubes were centrifuged for 5 seconds in an Eppendorf centrifuge, the supernatant was sampled and the beads were washed three times in 150 mM NaCl, 10 mM TRIS (pH 7.2). [³H]Nitrendipine was then measured using liquid scintillation counting in the initial supernatant (which represents the free [³H]nitrendipine) and in the washed beads (which represents the [³H]nitrendipine bound to monoclonal antibody XIIIE8₂/H8) Standard curves or tables of the natural log $B/B_o$ versus log X were calculated where B [³H]nitrendipine bound in the presence of X amount of unlabeled 1,4-dihydropyridine and $B_o$ is the [³H]nitrendipine bound in the absence of added 1,4-dihydropyridine. The average percent $B/B_o$ of the triplicate values of each sample and control was determined and the 1,4-dihydropyridine concentration from the sample or control $B/B_o$ value from the standard curve was also determined. The [³H]nitrendipine net counts per minute (CPM) and percent $B/B_o$ values are set forth in Table II.

TABLE II
Nifedipine Radioimmunoassay Using
Monoclonal Antibody XIIIE8₂/H8-Sepharose 6MB Beads

| Nifedipine Standard[a] (nanograms/ml) | Net CPM | % $B/B_o$[b] |
|---|---|---|
| — | 7830 | 100.0 |
| 3.7 | 8010 | 102.0 |
| 11.2 | 7708 | 98.2 |
| 18.7 | 6027 | 76.7 |
| 37.3 | 3998 | 50.9 |
| 112.0 | 1837 | 23.4 |
| 186.7 | 1138 | 14.5 |
| 373.4 | 677 | 8.6 |
| 1866.8 | 190 | 2.4 |

[a]Concentration of nifedipine standard in the final assay mixture.
[b]Defined in the text.

The results of a nitrenedipine radioimmunoassay using monoclonal antibody XH4₂/G1-Sepharose 6MB beads are set forth in Table III.

TABLE III
Nitrendipine Radioimmunoassay Using
Monoclonal Antibody XH4₂/G1-Sepharose 6MB Beads

| Nitrendipine Standard[a] (nanograms/ml) | Net CPM | % $B/B_o$[b] |
|---|---|---|
| 0 | 1908 | 100.0 |
| 0.4 | 2043 | 107.1 |
| 1.1 | 1676 | 87.8 |
| 1.8 | 1456 | 76.3 |
| 3.7 | 1149 | 60.2 |
| 11.0 | 717 | 37.6 |
| 18.3 | 535 | 28.1 |
| 37.4 | 333 | 17.5 |

[a]Concentration of nitrendipine standard in the final assay mixture.
[b]Defined in text.

Various radioactive $Ca^{2+}$ channel blockers at a 1.0 nM concentration were tested for their ability to bind to monoclonal antibody XIIIE8₂/H8-Sepharose 6MB beads. Table IV shows that the monoclonal antibody XIIIE8₂/H8-Sepharose 6MB beads were able to specifically bind [³H]nitrendipine, [³H]nimodipine, [³H]nifedipine-analog, [³H]PN200-110 (all 1,4-dihydropyridines) but the beads did not bind [³H]verapamil or [³H]diltriazem. [³H]nitrendipine gae the highest CPM's bound and the highest fmoles of radioactive 1,4-dihydropyridine bound per μg of monoclonal antibody XIIIE8₂/H8.

TABLE IV

| $Ca^{2+}$ Blocker (1.0 nM) | CPM Bound[a] | fmoles/μg[b] |
|---|---|---|
| [³H]Nitrendipine | 59103 | 33.8 |
| [³H]Nimodipine | 57439 | 20.9 |
| [³H]Nifedipine-Analog | 26000 | 18.8 |
| [³H]PN200-110 | 9419 | 4.8 |
| [³H]Verapamil | 234 | 0.2 |
| [³H]Diltiazem | 225 | 0.1 |

[a]Binding of various [³H]calcium channel blockers (1.0 nM) to monoclonal antibody XIIIE8₂/H8-Sepharose 6MB beads.
[b]fmoles of $Ca^{2+}$ channel blocker specifically bound per μg of monoclonal antibody XIIIE8₂/H8.

The affinity of the monoclonal antibodies of the present invention for [³H]nitrendipine was determined using a competitive binding assay according to the method of Muller (Muller, R., Methods in Enzylmology, 92, 589–601, 1983). The average apparent dissociation constant ($K_d$) of the [³H]nitrendipine-XIIIE8₂/H8-monoclonal antibody complex was calculated to be 26 nM. The average apparent dissociation constant ($k_d$) of the [³H]nitrendipine-XH4₂/G1 monoclonal antibody complex was calculated to be 12.5 nM.

What is claimed is:

1. 1,4-dihydropyridine immunogen conjugates of the formula:

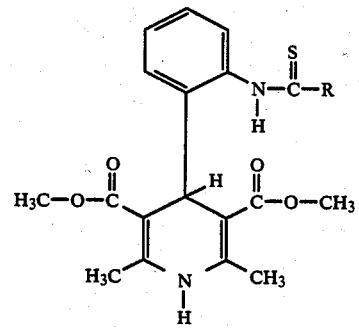

wherein R is bovine serum albumin, casein, ovalbumin or keyhole limpet hemocyanin.

2. An antibody prepared against the immunogen conjugate of claim 1.

3. The immunogen conjugate of claim 1 wherein R is keyhold limpet hemocyanin.

4. An antibody prepared against the immunogen conjugate of claim 3.

5. An antibody prepared against a 1,4dihydropyridine immunogen conjugate of the formula:

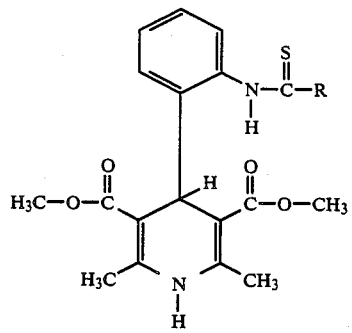

wherein R is a protein or polypeptide having a molecular weight of at least 4000.

6. An antibody prepared agasinst the immunogen conjugate of claim 5 wherein R is a protein having a molecular weight of at least 4,000.

7. A cell line having American Type Culture Collection accession number HB 8847.

8. A monoclonal antibody produced by a cell line having American Type Culture Collection accession number HB 8847.

9. A cell line having American Type Culture Collection accession number HB 8889.

10. A monoclonal antibody produced by a cell line having American Type Culture Collection accession number HB 8889.

11. In an immunoassay method for detecting the presence of 1,4-dihydropyridines, which function as calcium channel blockers, in a biological sample, the improvement comprising: employing an antibody of claims 5, 6, 2, 4, 8 or 10 as the antibody to said 1,4-dihydropyridines.

12. A method for detecting the presence of 1,4-dihydropyridines in a biological sample which comprises reacting said biological sample containing an unknown amount of a 1,4-dihydropyridine with a fixed amount of radiolabeled 1,4-dihydropyridine and a predetermined amount of the antibody of claims 6 2 4 8 10 and thereafter separating the resulting antigen-antibody complex from unbound antigen and measuring the radioactive content of either the complex or the unbound antigen.

13. The method of claim 12 wherein the radiolabeled 1,4-dihydropyridine is [$^3$H]nitrendipine.

14. A test kit for determining the presence of 1,4-dihydropyridines in a biological sample, which 1,4-dihydropyridines are capable of functioning as calcium channel blocking agents, which kit comprises at least one receptacle containing:
(a) one or more of a radiolabeled 1,4-dihydropyridine;
(b) an antibody specific for 1,4-dihydropyridines; and
(c) serial dilutions of 1,4-dihydropyridine standard solutions.

* * * * *